United States Patent [19]

Sarrine et al.

[11] Patent Number: 4,892,639
[45] Date of Patent: Jan. 9, 1990

[54] ELECTROPHORESIS PLATE AND METHOD OF MAKING SAME

[75] Inventors: Robert J. Sarrine, Beaumont; Philip A. Guadagno, Vidor; Henry A. Garsee, Kountze, all of Tex.

[73] Assignee: Helena Laboratories Corporation, Beaumont, Tex.

[21] Appl. No.: 74,584

[22] Filed: Jul. 17, 1987

[51] Int. Cl.[4] .................... G01N 27/28; G01N 27/26
[52] U.S. Cl. ............................. 204/299 R; 204/182.8
[58] Field of Search ............ 204/299 R, 182.8, 182.9, 204/182.7

[56] References Cited

U.S. PATENT DOCUMENTS

| | | | |
|---|---|---|---|
| 3,432,414 | 3/1969 | Rand | 204/249 R |
| 3,432,424 | 3/1969 | Zec | 204/182.7 |
| 3,479,265 | 11/1969 | Elevitch | 204/182.8 |
| 3,674,678 | 7/1972 | Post, Jr. et al. | 204/299 R |
| 3,751,357 | 8/1973 | Rains | 204/182.8 |
| 3,764,513 | 10/1973 | Saravis | 204/182.8 X |

FOREIGN PATENT DOCUMENTS 8704948  8/1987  PCT Int'l Appl. ............. 204/180.1

Primary Examiner—John F. Niebling
Assistant Examiner—John S. Starsiak, Jr.
Attorney, Agent, or Firm—Spencer & Frank

[57] ABSTRACT

An improved electrophoresis plate and method of making same includes a plate having an inert substrate and an electrophoretic medium formed on the substrate. The electrophoretic medium includes, as a part thereof, buffer blocks or buffer reservoirs, more specifically, relatively thick deposits of the electrophoretic medium. The electrophoretic medium buffer is positioned in a predetermined location relative to alignment apertures in the substrate.

The method of making the electrophoresis plate of the present invention includes priming the substrate with electrophoretic medium and thereafter forming, such as by casting or molding, the electrophoretic medium with the buffer blocks on the primed substrate.

19 Claims, 2 Drawing Sheets

ELECTROPHORESIS PLATE AND METHOD OF MAKING SAME

BACKGROUND OF THE INVENTION

The present invention relates to improvements in electrophoresis plates and methods of making such plates. By way of background, electrophoresis is a well-established method for separation of biochemicals, and is useful in the analysis of proteins found in complex physiological fluids and tissues. Typically, electrophoresis is carried out in a separation medium, such as a polymer gel, such as agarose or polyacrylamide. Of course, cellulose acetate is also used as a separation medium.

The gels are cast in molds and secured to a substrate. In the electrophoresis process, numerous samples are typically placed on the electrophoretic medium, i.e., the polymer gel. In order to cause the electrophoretic process to take place, an electric field is established with respect to the gel. To accomplish this, one common practice has been to immerse the opposite ends of the electrophoresis plate into reservoirs of electrically conductive buffers. The buffers are then connected to electrodes; the electrodes are connected respectively to the positive and negative terminals of a power supply to thus establish a voltage gradient across the electrophoresis plate. In response to the voltage gradient, the molecules in the samples migrate across the electrophoretic medium in proportion to various factors such as the charge and size of the protein molecules. Rather than immersing the ends of the electrophoresis plate into the buffers an alternate technique has been developed known as "wicking" in which an absorbent wick or piece of paper are used to connect buffers to their respective ends of the electrophoresis plate.

When the electrophoretic process has been completed, it is typical to place the electrophoresed sample under ultraviolet light. Normally, the gel (such as agarose gel) is essentially colorless, the inert plastic (typically polyester) or glass substrate was transparent, and a piece of dark or black paper would be placed under the substrate such that ultraviolet light would cause the sample to fluoresce, greater optical contrast would be provided by the paper such that the results of the electrophoresis could be more easily determined and interpreted.

The present invention provides numerous benefits with respect to the electrophoresis plate and the method of making and using the same, as will be hereinafter described.

SUMMARY OF THE INVENTION

The present invention provides, as a first benefit, for the elimination of external buffer reservoirs by the use of buffer blocks, i.e., substantial amounts or volumes of buffer formed as part of the gel or coating on the substrate itself. In this fashion, the individual electrophoresis plate includes self-contained buffer reservoirs. When the electrophoretic medium is a polymer, the buffer reservoirs are in the form of additional polymer gel.

Yet another feature of the present invention is that when the electrophoresis plate having the samples thereon is placed in an electrophoresis apparatus and subjected to the voltage gradient as previously described, it is desirable to properly align external electrodes relative to the samples, such that each sample is subjected to the same voltage gradient. Stated another way, it is desirable that the positive and negative electrodes be parallel to each other and that the plurality of samples be positioned intermediate the two electrodes and parallel to the axes of the electrodes. The present invention provides alignment holes in the substrate which, although the provision of alignment holes per se is old, provide the additional benefit and advantage of permitting alignment during the formation of the buffer blocks, thus ensuring that the buffer blocks are properly aligned relative to the electrodes. In the event that built-in electrodes are utilized, the present invention aids in proper alignment of the built-in electrodes and the buffer blocks.

The present invention provides, as part of the new and improved electrophoresis plate, the use of a non-transparent, preferably black non-translucent substrate, thus providing better optical contrast when the electrophoresed plate is placed under the ultraviolet light such that the results of electrophoresis may be better determined. The use of a black substrate, of course, is not necessary if the electrophoresed sample is to be subjected to visible light rather than ultraviolet light.

The method of making the electrophoresis plates of the present invention includes the conventional step of priming the inert substrate and providing alignment holes and thereafter providing the electrophoretic coating and buffer blocks properly positioned relative to the alignment holes.

The various features and benefits of the present invention will become more apparent upon reading the following detailed description of the invention taken in conjunction with the drawings.

BRIEF DESCRIPTION OF THE DRAWINGS

In the drawings wherein like reference numerals identify corresponding parts.

DETAILED DESCRIPTION OF THE INVENTION

Referring first to the electrophoresis plate 10 of the present invention, the plate includes a substrate 12 of a substance which is both electrically and chemically inert. The substrate should be formed of one of many materials that are used as supports for electrophoretic gel media and have the desired degree of rigidity to thus protect the gel from damage during handling and shipment. Film materials that are suitable for this purpose include polystyrene, polyethylene and glass, as well as polyesters. A preferred substrate is a polyester film sold by E. I. duPont DeNemours and Company under the trademark Mylar and, more particularly, dark or black Mylar is preferred. An alternative would be a thermoplastic polycarbonate film sold by General Electric under their trademark Lexan. Again, the film should be dark or black if the electrophoresed sample is to be evaluated under ultraviolet light.

The following explanation will be given assuming that agarose gel is to be used as the electrophoretic medium. However, it should be understood that, according to the principles of the present invention, other electrophoretic media may be used.

Figure 1:
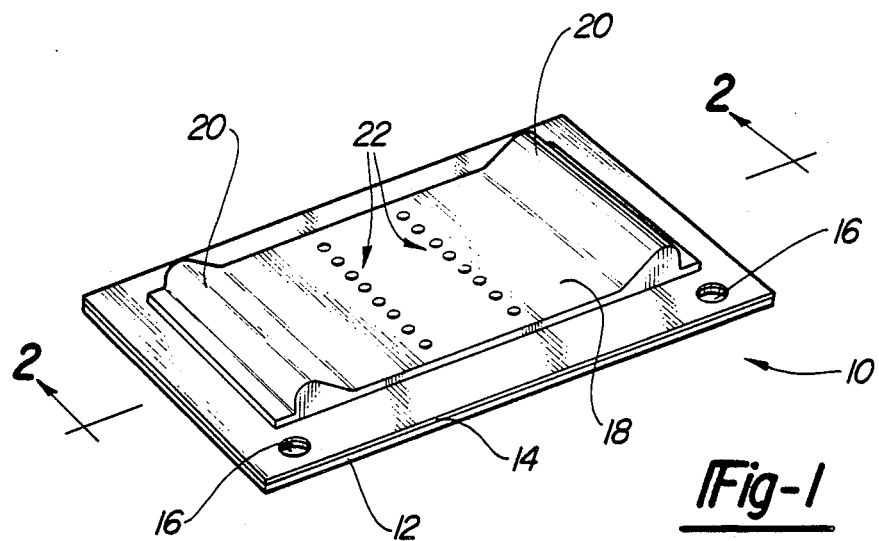
FIG. 1 is a perspective illustration of an electrophoresis plate made in accordance with the principles of the present invention.
Figure 2:
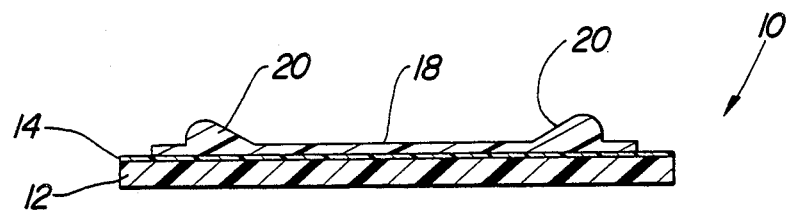
FIG. 2 is a cross-sectional illustration of the electrophoresis plate of the present invention taken in the direction of arrows 2—2 of FIG. 1.

Continuing to refer to FIGS. 1 and 2, before or after the substrate is coated with a primer film or layer 14 of electrophoretic gel media, a pair of alignment holes 16 may be provided. These alignment holes are illustrated as being adjacent one edge of the plate 10. The number of alignment holes and their precise location may, of course, be varied within the spirit of the present invention. Then, an electrophoretic gel layer 18 is formed, such as by casting, with the electrophoretic gel 18 covering substantially all of the surface area of the primed substrate. The electrophoretic gel may be cast or molded in place in the general configuration of a large rectangle with extra-thick members 20 at opposite ends of the plate. These extra-thick members 20 are referred to as buffer blocks, and they extend upwardly a substantial distance from the plate, relative to the thickness of the electrophoretic layer 18, extend essentially the full width of the electrophoretic layer 18, and are of substantial width in the longitudinal direction. These buffer blocks provide the buffer reservoir for the electrophoresis.

In a typical system, a primer layer 14 may be several microns thick, the electrophoretic layer 18 may be 20–25 mm thick (1 mm=25.4 microns), and the buffer blocks may be about 40 mm thick, the 40 mm being in addition to the 20–25 mm thickness of the film 18. The film 18 may also be provided with a series of sample apertures 22. In the embodiment of FIG. 1, two series of apertures 22 are provided. The sample apertures are aligned perpendicular to the elongated axis of the plate 10 and parallel to the axes of the buffer blocks 20.

The substrate is typically rectangular in configuration and is corona-charged to accept a liquid gel. It should be understood that in the first instance the substrate is chemically and electrically inert, and thus the electrophoretic layer would not form a suitable coating or layer, but would rather form a series of discrete droplets on the surface of the substrate. Thus, the use of a corona charge on the substrate to allow adherence of the electrophoretic layer and allow the layer to gel is a common technique, referred to as priming the substrate.

Figure 3:
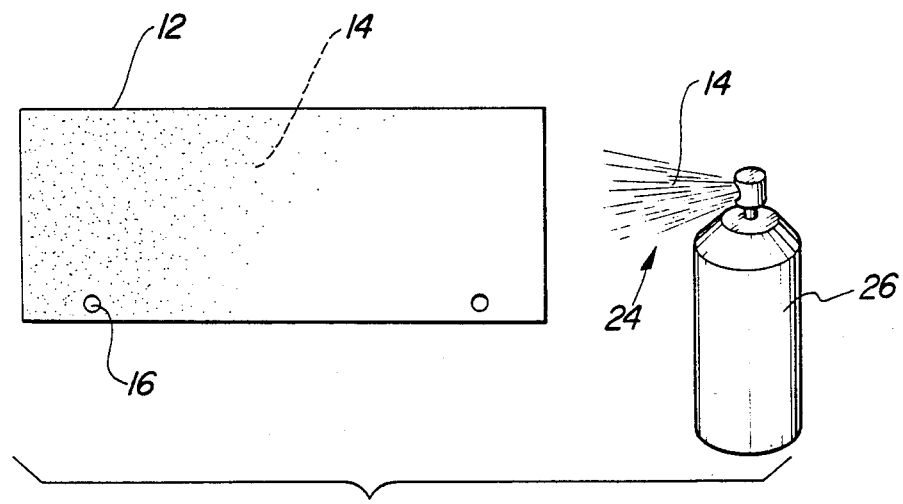
FIG. 3 is a diagrammatic illustration of priming the inert substrate.

Referring next to FIG. 3, a first step in the method of making the electrophoresis plate of the present invention will thus be described. A substrate 12 is illustrated in FIG. 3 and, diagrammatically, the gel is illustrated as being applied via a spray 24 from a container 26. The primer layer may be the same electrophoretic medium as the subsequent electrophoretic gel layer although more dilute. It should be understood that this is diagrammatic only and, in FIG. 3, the primer 14 is illustrated as covering the substrate. It is common to prime an electrophoresis plate, such as by as spray technique, or alternatively, by dipping the substrate in a dilute solution and thereafter removing excess via a squeegee or the like. The primer layer is allowed to cure or gel. Then, alignment holes 18 may be provided in the substrate 12. (Alternatively, alignment holes may be provided prior to priming.) If "built-in" electrodes are desired they may be placed on the substrate prior to the application of the primer 14.

Figure 4:
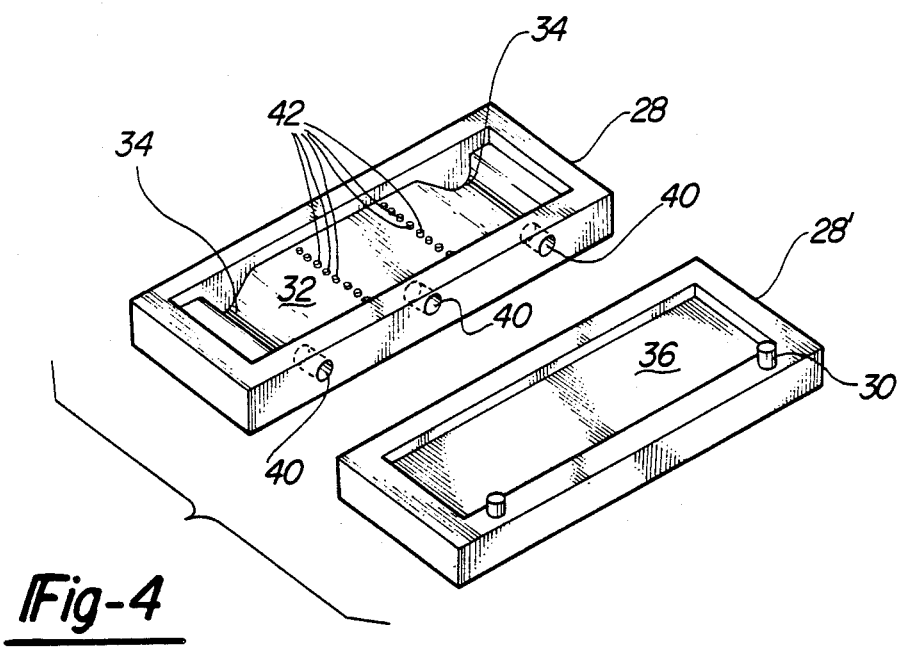
FIG. 4 is an illustration of a mold for casting or coating the gel layer and buffer blocks onto the primed substrate.

Referring next to FIG. 4, an upper and lower press mold halves 28, 28' respectively, are illustrated, each having a generally rectangular configuration. A pair of pins 30 extend upwardly from the top surface of the lower mold half 28', to be received within the alignment holes in the plate. The upper mold half 28 has a generally rectangular mold cavity 32 and, at each end of the cavity 32, enlarged cavity portions 34. The lower mold half 28' has a generally rectangular mold cavity 36 aligned under the mold cavity 32. With a primed substrate on top of the lower mold half, the upper mold half 28 is brought down on top of the substrate. The pins 30 extend through the alignment holes 16. The electrophoretic medium would be placed within the mold cavity such as through inlets 40 in the wall of the upper mold half and the mold is pressed, thus forming a one-piece casting on top of the primed layer 14. The one-piece casting thus includes the electrophoretic film 18 with the integral buffer blocks 20 formed at opposite ends thereof. Shallow pins 42 in the upper mold cavity provide the apertures 22 for the samples.

Figure 5:
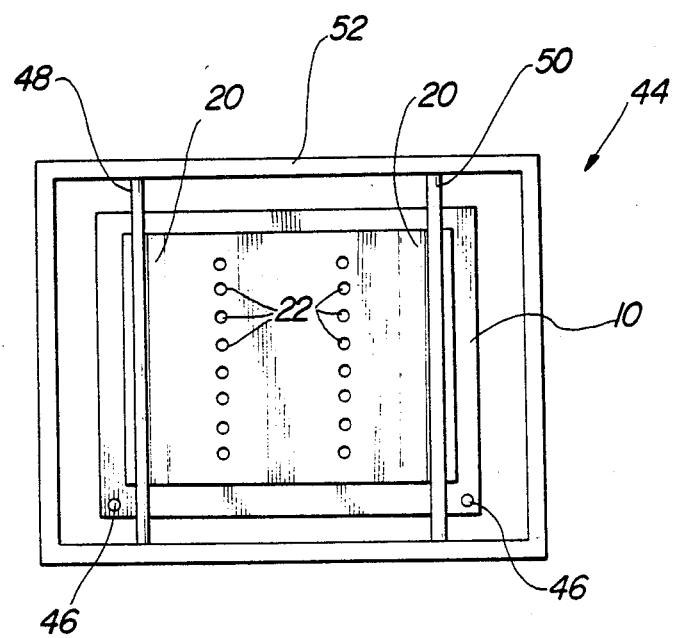
FIG. 5 is a plan view of a typical electrophoretic chamber illustrating the electrodes properly aligned relative to the buffer blocks through the use of the alignment holes.

After the electrophoretic film cures or gels, the plate 10 is removed from the mold. After the samples are placed in the apertures 22, the assembly is placed in an electrophoretic chamber illustrated somewhat diagrammatically in FIG. 5. As fully illustrated in FIG. 5, the electrophoretic chamber 44 includes alignment pins 46 extending upwardly from the base of the chamber with the alignment pins extending through the apertures or alignment holes 16 in the electrophoresis plate 10. With the alignment pins properly positioned within the alignment holes, the buffer blocks 20 will be properly aligned under the electrodes 48, 50 within the electrophoretic chamber 44. The electrodes are shown as attached to one wall 52 of the chamber 44. During electrophoresis, buffer gel moves from one block, across the plate, toward the other block. By having proper alignment of the electrodes relative to the buffer blocks, the potential gradient will remain constant across the full width of the electrophoresis plate and sufficient buffer will be provided across the full width of the plate such that the results may be relied upon.

The foregoing is a complete description of the preferred embodiment of the present invention. Various changes may be made without departing from the spirit and scope of the present invention. Hence, the present invention should be limited by the following claims.

What is claimed is:

1. In an electrophoresis plate of the type including a substrate which is chemically and electrically inert, relative to electrophoretic separation, and a layer of electrophoretic medium thereon, the electrophoretic medium including at least some buffer material, the electrophoretic medium including upper and lower surfaces, the lower surface of the electrophoretic medium being in contact with said substrate, the improvement comprising:

alignment means associated with the electrophoresis plate; and
buffer blocks formed integrally with the electrophoretic medium and spatially oriented in a predetermined position relative to the alignment means, said buffer including material for functioning as a self-contained reservoir;

said buffer blocks extending from said upper surface of the electrophoretic medium in a direction away from said substrate.

2. The invention as defined in claim 1 wherein said substrate is black in color for providing color contrast of a sample electrophoresed thereon.

3. The invention as defined in claim 1 wherein said substrate provides color contrast of a sample electrophoresed thereon relative to ultraviolet fluorescence.

4. The invention as defined in claim 1 wherein said substrate is formed of black polyester film for providing color contrast of a sample electrophoresed thereon.

5. The invention as defined in claim 1 wherein the electrophoresis plate includes a primer coat of electrophoretic medium intermediate the substrate and the electrophoretic layer.

6. The invention as defined in claim 1 wherein said electrophoretic medium is agarose.

7. The invention as defined in claim 1 wherein said buffer blocks are substantially thick relative to the thickness of the electrophoretic medium.

8. The invention as defined in claim 1 wherein said buffer blocks extend substantially the full width of the substrate.

9. The invention as defined in claim 1 wherein said buffer blocks are free of electrodes.

10. The invention as defined in claim 1 wherein said inert substrate is essentially in a single plane.

11. The invention as defined in claim 1 wherein said buffer blocks are substantially parallel to each other.

12. The invention as defined in claim 1 wherein said alignment means includes at least one aperture in said electrophoresis plate.

13. A method of forming an electrophoresis plate of the type including a substrate and a layer of electrophoretic medium associated therewith, the electrophoretic medium including at least some buffer material comprising the steps of:
   providing alignment apertures in said substrate;
   forming a layer of electrophoretic medium on said substrate; and
   forming buffer blocks on said substrate, the electrophoretic medium including upper and lower surfaces, the lower surface of the electrophoretic medium being in contact with said substrate, said buffer blocks being aligned in a predetermined orientation substantially parallel to each other relative to said alignment apertures, said buffer blocks including buffer material for functioning as a self-contained reservoir;
   said buffer blocks extending from said upper surface of the electrophoretic medium in a direction away from said substrate.

14. The invention as defined in claim 13 wherein said buffer blocks are formed on said substrate simultaneously with the formation of the electrophoretic medium.

15. The method of claim 13 and including applying a primer layer of electrophoretic medium on said substrate.

16. The method as defined in claim 15 wherein said alignment holes are formed subsequent to priming said substrate.

17. The method as defined in claim 13 wherein said substrate is non-transparent and non-translucent.

18. The method as defined in claim 13 wherein said substrate is formed of a darkened colored inert material for providing color contrast of a sample electrophoresed thereon.

19. In an apparatus for conducting electrophoretic analysis including a base for supporting an electrophoretic plate and at least one electrode spaced apart from the base, said electrophoretic plate including at least a layer of electrophoretic medium thereon, the electrophoretic medium including upper and lower surfaces, the lower surface of said electrophoretic medium being in contact with said substrate, the improvement comprising:
   buffer blocks formed integrally with the electrophoretic medium and spatially oriented in a predetermined position relative to said at least one electrode, said buffer blocks including buffer material for functioning as a self-contained reservoir,
   said buffer blocks extending from said upper surface of the electrophoretic medium in a direction away from said substrate.

* * * * *